(12) United States Patent
Witham et al.

(10) Patent No.: US 6,670,626 B2
(45) Date of Patent: Dec. 30, 2003

(54) DEVICE TO DISINFECT AIR OR SURFACES WITH RADIATION AND METHOD THEREFOR

(75) Inventors: David L. Witham, Ventura, CA (US); Robert Arrance, Valencia, CA (US)

(73) Assignee: UltraViolet Devices, Inc., Valencia, CA (US)

( * ) Notice: Subject to any disclaimer, the term of this patent is extended or adjusted under 35 U.S.C. 154(b) by 0 days.

(21) Appl. No.: 10/183,780

(22) Filed: Jun. 25, 2002

(65) Prior Publication Data

US 2003/0001113 A1 Jan. 2, 2003

Related U.S. Application Data

(60) Provisional application No. 60/301,903, filed on Jun. 29, 2001.

(51) Int. Cl.[7] .................................................. A61L 2/10
(52) U.S. Cl. ................................ 250/504 R; 250/493.1
(58) Field of Search ........................ 250/504 R, 494.1, 250/492.1, 522.1, 432 R, 436

(56) References Cited

U.S. PATENT DOCUMENTS

| 4,494,350 A | 1/1985 | Sharp ........................... 52/665 |
| 5,207,074 A | 5/1993 | Cox et al. ...................... 62/285 |
| 5,322,569 A | 6/1994 | Titus et al. ..................... 134/1 |
| 5,492,557 A | 2/1996 | Vanella .......................... 96/16 |
| 6,074,748 A | 6/2000 | Ogata .......................... 428/357 |
| 2002/0045369 A1 | 4/2002 | Agro ........................... 439/121 |

*Primary Examiner*—John R. Lee
*Assistant Examiner*—Christopher M. Kalivoda
(74) *Attorney, Agent, or Firm*—Cislo & Thomas LLP

(57) ABSTRACT

Interlocking, modular anti-microbial Radiation fixtures mount on a custom rack or bracket, which are used to irradiate an air stream and/or surfaces within an HVAC (heating, ventilating, air conditioning) system. The individual units are adapted for modular integration and slidable mounting on a rack, bracket or fixture which allows for ease of installation.

11 Claims, 4 Drawing Sheets

DEVICE TO DISINFECT AIR OR SURFACES WITH RADIATION AND METHOD THEREFOR

CROSS-REFERENCE TO RELATED APPLICATIONS

This patent application is related to U.S. Provisional Patent Application Ser. No. 60/301903 filed Jun. 29, 2001 for DEVICE TO DISINFECT AIR OR SURFACES WITH UV LIGHT AND METHOD THEREFOR, which application is incorporated herein by this reference thereto.

FIELD OF THE INVENTION

This invention relates to anti-microbial radiation fixtures within HVAC equipment.

BACKGROUND OF THE INVENTION

This invention relates to modular, anti-microbial radiation fixtures that may be positioned in tandem to provide adequate radiation coverage of large areas as may be found in heating, ventilating and air conditioning systems. Previous approaches have entailed using hard wired fixtures, with the necessity for many wires and cable running throughout the installation, or complex and expensive connection methods. The fixtures are generally mounted on a support structure within the equipment.

SUMMARY OF THE INVENTION

This invention consists of interlocking, modular anti-microbial radiation fixtures that mount on a custom rack or bracket, which in turn are used to irradiate an air stream and/or surfaces within an HVAC (heating, ventilating, air conditioning) system such as filter elements, air conditioning coils, drip pans and duct wall surfaces, thereby reducing the formation of molds and fungus on those surfaces. The operating fixtures may also reduce fungi, bacteria and virus in a moving air stream within which they are used. The invention may utilize inexpensive electrical connections in combination with a simple mechanical locking method. Each module engages mechanically and electrically with the next one and the desired coupled component is in turn slid into position on a rack support or bracket with final connection to power being in the form of a cable which plugs into the last unit of the set.

OBJECTS OF THE INVENTION

It is an object of the present invention to provide interlocking, modular anti-microbial radiation fixtures that mount on a custom rack or bracket.

It is another object of the present invention to provide a means of having modular fixtures that are positioned in tandem and which may be combined to adequately cover a large variety of applications.

It is still another important object of the invention to provide a modular anti-microbial radiation fixture that may be connected in tandem fashion with a like fixture so as to provide an assembled fixture for a variety of end uses and applications.

It is still another important, specific object of the invention to provide radiation fixture modules that are integrateable to form a specific designed fixture in cooperation with a bracket or rack wherein the assembled device may have a wide application of uses.

These and other objects and advantages of the present invention will be apparent from a review of the following specification and accompanying figures.

DESCRIPTION OF THE PREFERRED EMBODIMENT(S)

The detailed description set forth below in connection with the appended figures is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

This invention consists of modular, anti-microbial radiation fixtures and support structures upon which to mount them.

The modular fixtures each share a common design and many details, but differ in length and electrical conponentry to accommodate lamps of various outputs. Modules may be combined to adequately cover a large variety of applications. The modules incorporate integral slots that match the configuration of the rack or bracket. Each module is slid onto the rack or bracket while the next or successive module is slid onto the rack and a connection is made to the previous module with a mating connector and retaining latch. As each module is positioned and connected, the assembly is pushed further down the rack or bracket. When the final module is in place, a power supply is connected to the last exposed module receptacle. The power cable is then connected to the power supply. The power supply can be a flexible utility cord or a conduit box to accept permanent hard wiring.

Figure 1:
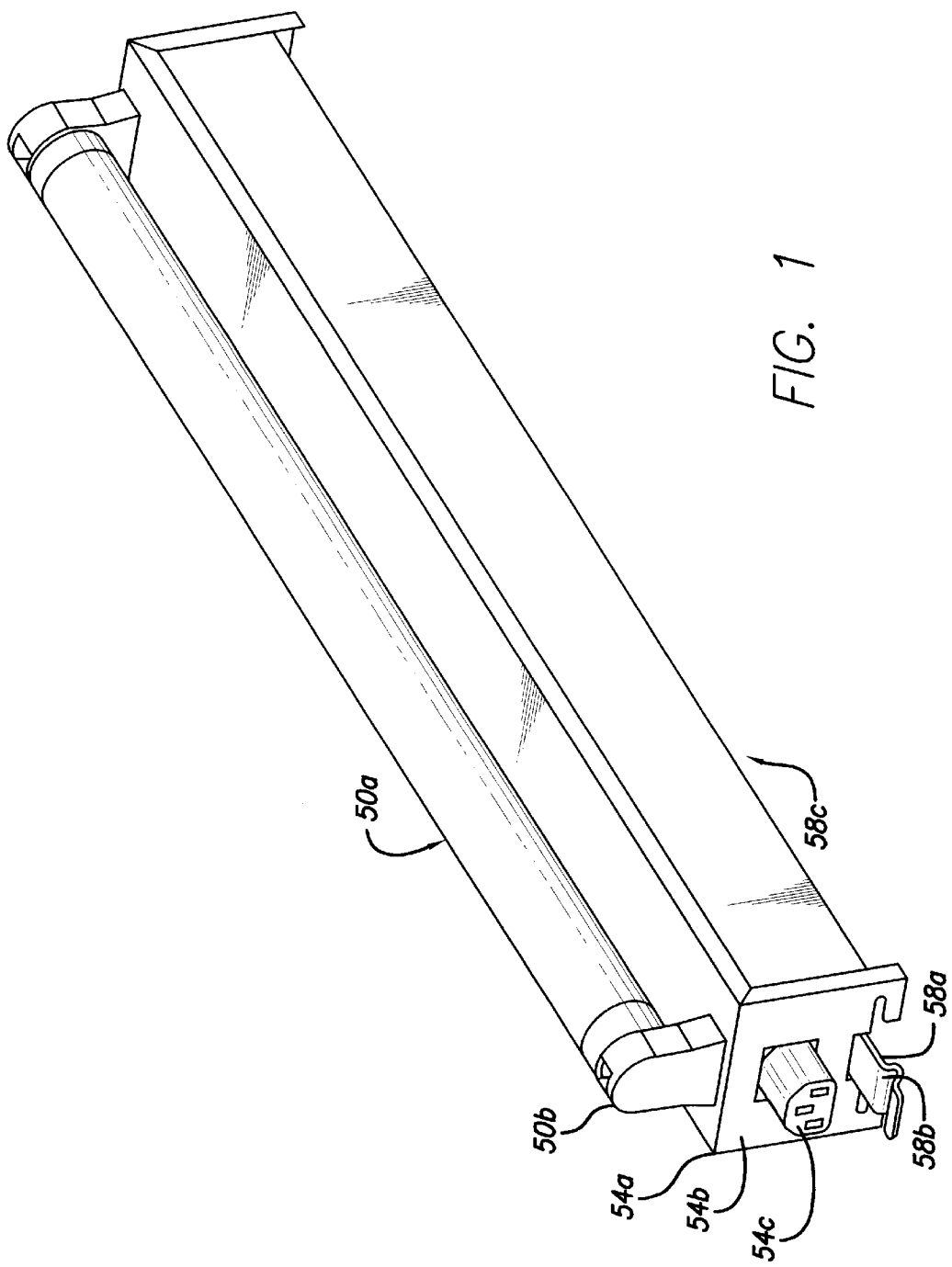
FIG. 1.: A typical fixture of this invention.

Referring to the figures, FIG. 1 illustrates a typical fixture of the invention from a side perspective. Radiation bulb 50a may be an ultraviolet light, or any other radiation-emitting device selected for a particular anti-microbial application. Receptacle 50b is typically configured to receive a conventional 2-prong connector, but may be of any configuration known in the art.

Socket 54c is depicted here as a 3-prong inlet, however any conventional electrical connection can be used. Locking tang 58a comprises a longitudal member with a downward bias, and includes a vertical protrusion 58b for locking engagement with an appropriately configured slot. Locking tang 58a extends through tang cavity 58c.

Figure 2:
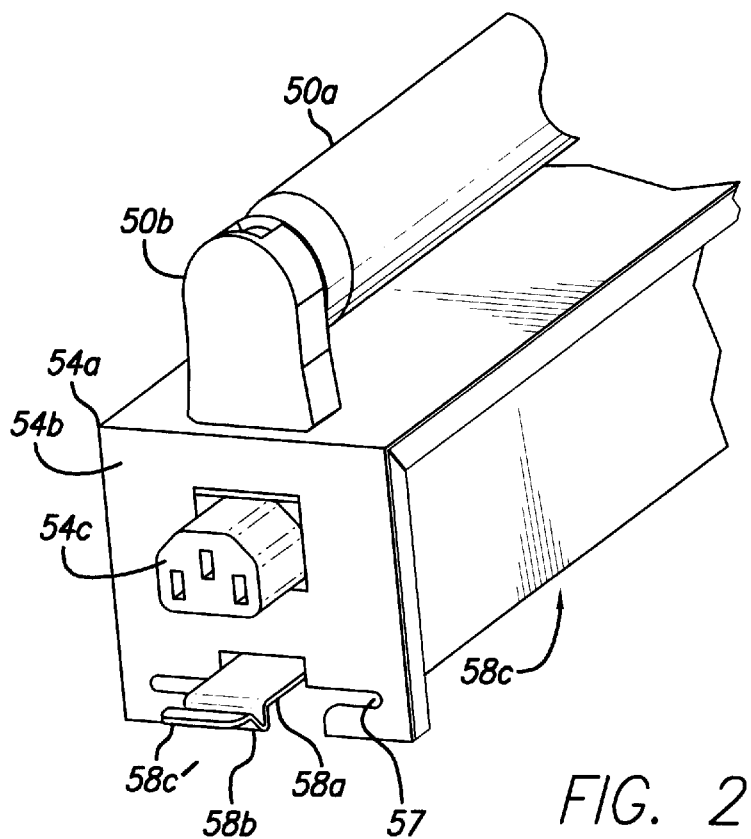
FIG. 2.: A detail showing one end plug and mechanical latch for inter-connecting the units both mechanically and electrically.
Figure 3:
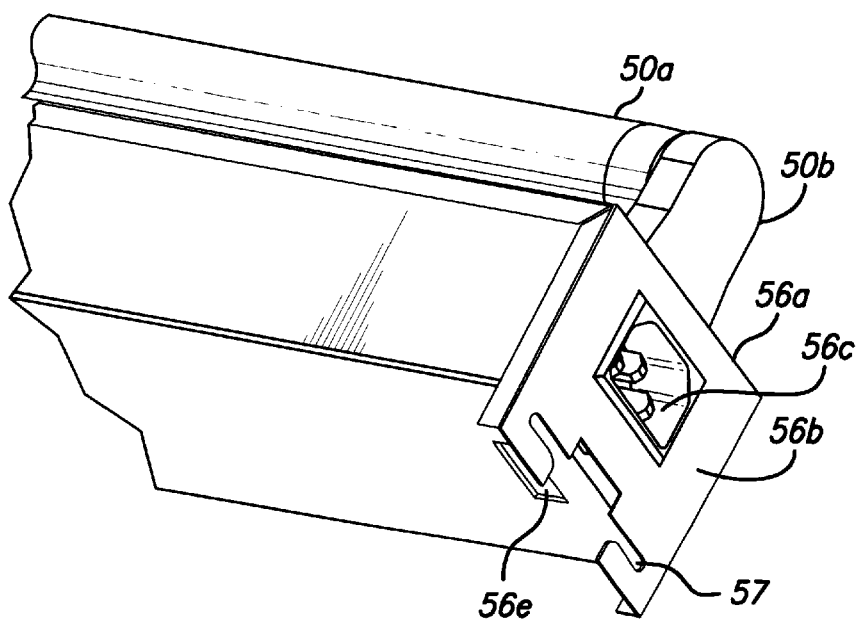
FIG. 3.: An enlarged detail showing the opposite end connection from that illustrated in FIG. 2 and depicting slots for track mounting.

FIGS. 2 and 3 show enlarged details of the plug and socket sides of an embodiment of this invention. In FIG. 3, the electrical connection 56c is depicted as a recessed plug, although any conventional electrical connection can be used.

Figure 4:
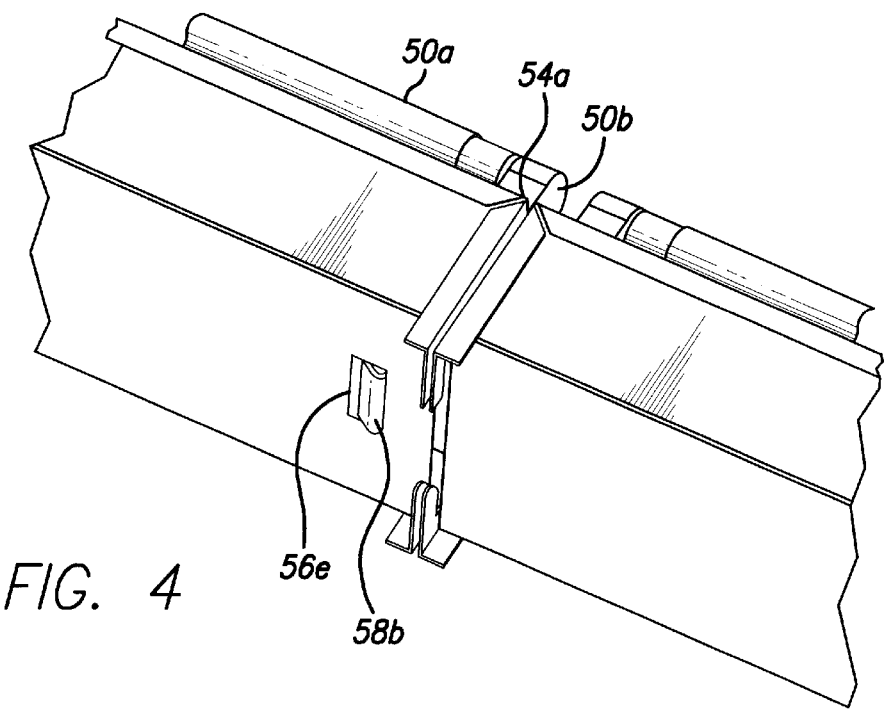
FIG. 4.: A detail showing two of the modular units inter-connected end to end or in tandem.

FIG. 4 depicts two modular units in tandem engagement. As shown in FIG. 4, vertical protrusion 58b lockingly engages slot 56e, and lip 58c (not visible) rests on the surface adjacent to slot 56e in flush contact.

Figure 5:
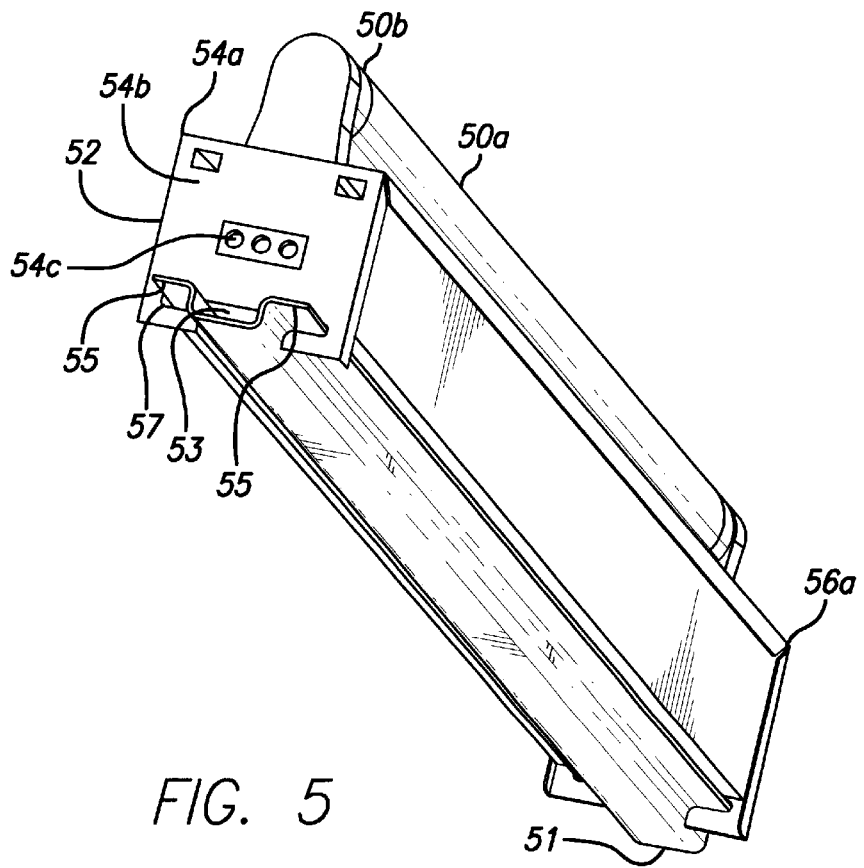
FIG. 5.: A typical fixture mounted on a typical track or mounting bracket.

Referring to FIG. 5, the anti-microbial radiation system of the present invention, includes at least one support track 51, the support track having a generally concave cross-section 53 and including outer edge protrusions 55 that extend laterally to form wings for slideable engagement with a lateral groove 57. The support track 51 may be formed from a wood, metal, composite or polymeric material, and is configured to support or suspend the system from a surface, such as a wall, ceiling or floor. The track 51 may be attached to the desired surface by conventional means, such as bolts, nails, wires, adhesives, or any other suitable method. Frame 52 includes a first end 54a, with a first face 54b that includes a modular socket 54c, and a second end 56a, with a second face 56b that includes a modular plug 56c, best shown in FIG. 3. The faces 54a and 56a define lateral grooves 57 for slideably receiving lateral wings 55 for suspending the system, and the ends also include slots 56e, best shown in FIG. 3, and locking tangs 58a, best shown in FIG. 1 or 6, for engagement with slots 56e. Locking tangs 58a include vertical protrusions 58b, and locking tang 58a is biased so that vertical protrusions 58b snap into engagement with slots 56e in a secure manner, as shown in FIG. 4. Locking tangs 58a are attached to frame 52 by anchoring structure 61, best shown in FIG. 6. Anchoring structure 61 is depicted as including plurality of apertures for receiving fastening devices, such as bolts, but can comprise any conventional anchoring method known to those skilled in the art. Ultraviolet light 50a is removeably attached to a frame in a conventional manner, although the system can accommodate any radiation-emitting device.

Figure 6:
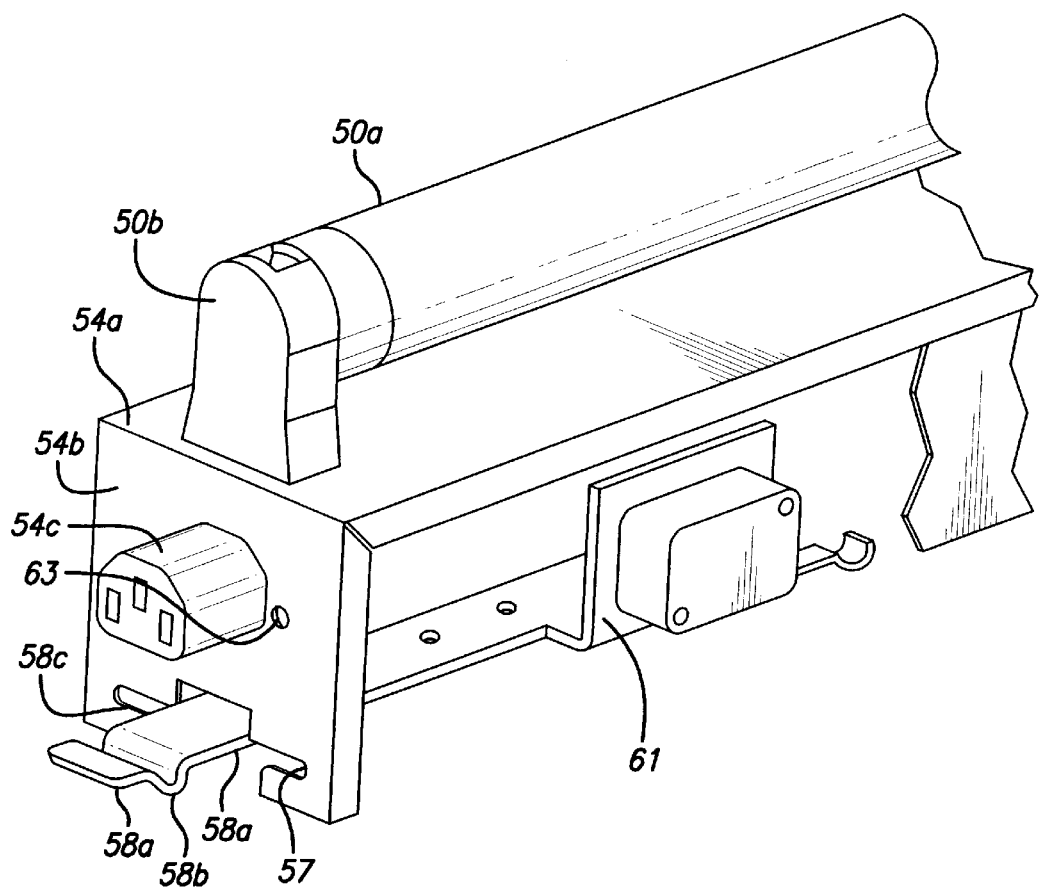
FIG. 6.: Provision for an interlock switch which prohibits operation unless the unit is mounted on the appropriate track.

FIG. 6 illustrates an embodiment of the invention that includes an interlock switch 63. When the invention is connected in tandem with another module, locking tang 58a rests below cavity 58c due to its downward bias. When support track 51 is engaged within lateral grooves 57, track 51 forces locking tang 58a upward into cavity 58c. When locking tang 58a is forced upward, it depresses interlock switch 63, which closes the circuit that provides power from electrical connection 54c to radiation device 50a, which may be an ultraviolet light. When track 51 is not properly engaged, locking tang 58a remains in its natural downward bias, interlock switch 63 remains extended, and the circuit is open, which prevents operation of the device.

In operation, light 50a is removeably attached to receptacle 50b, and frame 52 is placed in sliding relationship with track 51 by grooves 57. Subsequent frames are connected with tracks in a similar manner, and the separate fixtures are interconnected by inserting a plug 56c into a corresponding socket 54c, in addition to engaging locking tangs 58a with slots 56e. An external power source may then be connected to an exposed electrical coupling, such as modular socket 54c, to energize the system. Locking tang 58a depresses interlock switch 63, which closes the circuit and allows locking tang 58a to flow to the light.

While the present invention has been described with regards to particular embodiments, it is recognized that additional variations of the present invention may be devised without departing from the inventive concept.

What is claimed is:

1. An anti-microbial radiation system, comprising:
    a track;
    a plurality of modular fixtures retentively engaging the track, said modular fixtures each having at least one integrated mechanical and electrical coupling end portions whereby a plurality of modular fixtures may be selectably interconnected by detachable attachment; said modular fixtures being electrically connected in cascaded arrangement, adjacent ones of said modular fixtures having said end portions respectively thereof releasably interlocked one with the other; and,
    a plurality of radiation sources each coupled to one of said modular fixtures for actuation thereby.

2. The anti-microbial radiation system of claim 1 wherein said track receives the modular fixtures in sliding relationship therewith, and wherein one modular fixture is mechanically and electrically connected to successively placed modular fixtures which are in sliding relationship to said track, whereby a selected number of modular units may be interposed in a space to be exposed to radiation.

3. The anti-microbial radiation system of claim 2, wherein said end portions include two vertical surfaces, said vertical surfaces each including an opening that defines a channel for receiving said track.

4. The anti-microbial radiation system of claim 3, wherein each modular fixture includes at least one horizontal surface, said horizontal surface including at least one integral slot, and at least one mechanical coupling configured for locking engagement with said integral slot.

5. The anti-microbial radiation system of claim 4 wherein the electrical couplings are disposed upon the vertical surfaces.

6. The anti-microbial radiation system of claim 5 wherein the electrical couplings comprise a socket, and a plug.

7. The anti-microbial radiation system of claim 6 wherein the mechanical coupling comprises a longitudinal member.

8. The anti-microbial radiation system of claim 7 wherein the longitudinal member includes a horizontal part and a protrusion extending vertically therefrom.

9. The anti-microbial radiation system of claim 8 wherein the channel is defined by a portion of the vertical surface extending below the at least one horizontal surface.

10. An anti-microbial light system, comprising:
    at least one support track, said support track having a generally concave cross-section, and including outer edge protrusions that extend laterally to form wings for slideable engagement with a lateral groove, at least one frame, said frame including a first end, with a first face including a modular socket, and a second end, with a second face including a modular plug, said faces defining lateral grooves for slidably receiving lateral wings for suspending the system, and said ends including slots, and locking tangs for engagement with said slots, and
    at least one ultra-violet light, each light being removably attached to a frame.

11. A method of providing radiation devices in hard to reach places comprising the steps of:
    creating selectably interconnected detachably attachable modules for association with a bracket or rack wherein a selected number of modules are placed in sliding relationship with said rack or bracket to be retentively engaged thereby, and the number of modules being interconnected to provide satisfactory treatment of the surface or area to be treated by radiation;
    electrically connecting the modules in cascaded arrangement, adjacent ones of the modules having adjoining ends releasably interlocked one with the other.

* * * * *